US005383855A

United States Patent [19]

Nicholson et al.

[11] Patent Number: 5,383,855

[45] Date of Patent: Jan. 24, 1995

[54] ELECTRONICALLY MONITORED ANGIOPLASTY SYSTEM

[75] Inventors: Warren B. Nicholson, Dublin; Mark D. Pfouts, Powell; Russell I. Delong, Columbus, all of Ohio

[73] Assignee: Medex, Inc., Hilliard, Ohio

[21] Appl. No.: 932,645

[22] Filed: Aug. 20, 1992

[51] Int. Cl.[6] ................ A61M 29/00

[52] U.S. Cl. ................ 604/100; 604/97; 73/4 R

[58] Field of Search ................ 604/96-103; 606/192-195; 73/4 R

[56] References Cited

U.S. PATENT DOCUMENTS

Re. 33,360 10/1990 Reynolds et al. .
984,839 2/1911 Neiman .
2,745,575 5/1956 Spencer .
2,874,877 2/1959 Spencer .
3,353,718 11/1967 McLay .
3,698,381 10/1972 Federico et al. .
3,703,099 3/1973 Rouse .
3,720,199 3/1973 Rishton et al. .
3,893,452 7/1975 Birnbaum .
3,985,123 10/1976 Herzlinger et al. .
4,003,370 1/1977 Emil et al. .
4,006,736 2/1977 Kranys et al. .
4,016,871 4/1977 Schiff .
4,080,966 3/1978 McNally et al. .
4,231,366 11/1980 Schael .
4,332,254 6/1982 Lundquist .
4,342,218 8/1982 Fox .
4,370,982 2/1983 Reilly .
4,392,849 7/1983 Petre et al. .
4,439,185 3/1984 Lundquist .
4,446,715 5/1984 Bailey .
4,457,751 7/1984 Rodler .
4,478,222 10/1984 Koning et al. .
4,522,194 6/1985 Normann .
4,557,269 12/1985 Reynolds et al. .
4,583,974 4/1986 Kokernak .
4,600,015 7/1986 Evans et al. .
4,601,037 7/1986 McDonald .
4,651,738 3/1987 Demer et al. .
4,655,749 4/1987 Fischione .
4,658,829 4/1987 Wallace .
4,670,006 6/1987 Sinnett et al. .
4,672,974 6/1987 Lee .
4,697,574 10/1987 Karcher et al. .
4,706,670 11/1987 Andersen et al. .
4,723,556 2/1988 Sussman .
4,723,938 2/1988 Goodin et al. .

(List continued on next page.)

FOREIGN PATENT DOCUMENTS

WO8503007 7/1985 WIPO .
WO9004987 5/1990 WIPO .
WO9011040 10/1990 WIPO .

OTHER PUBLICATIONS

International Search Report, Mailed Oct. 29, 1993 PCT/US93/06065.
Exhibit D-1; USCI Wizard Disposal Inflation Device Sales Brochure.

*Primary Examiner*—C. Fred Rosenbaum
*Assistant Examiner*—Mark Bockelman
*Attorney, Agent, or Firm*—Wood, Herron & Evans

[57] ABSTRACT

An electronically monitored angioplasty system is provided with a verifier circuit to verify the operation of conversion circuitry for converting an electrical pressure signal from a pressure transducer to a displayed numerical value on a digital read-out. The verifier circuit is selectively activated to offset the displayed numerical value by a predetermined amount and upon deactivation the displayed numerical value returns to the pressure sensed by the pressure transducer in the balloon. In one embodiment, a reference signal to the conversion circuitry is selectively offset by a signal corresponding to the predetermined amount and in another embodiment the electrical pressure signal itself is selectively offset by a reference signal corresponding to the predetermined amount. In another aspect of the system, an audible balloon deflation indicator circuit sounds a pleasant signal that the pressure within the balloon has fallen below a threshold pressure so the doctor need not divert attention from the patient.

17 Claims, 4 Drawing Sheets

U.S. PATENT DOCUMENTS 4,743,230 5/1988 Nordquest .
4,758,223 7/1988 Rydell .
4,760,730 8/1988 Frank et al. .
4,781,192 11/1988 Demer .
4,815,472 3/1989 Wise et al. .
4,832,692 5/1989 Box et al. .
4,854,324 8/1989 Hirschman et al. .
4,858,615 8/1989 Meinema .
4,872,483 10/1989 Shah .
4,877,035 10/1989 Bogen et al. .
4,886,070 12/1989 Demarest .
4,896,671 1/1990 Cunningham et al. .
4,899,741 2/1990 Bentley et al. .
4,901,735 2/1990 Von Berg .
4,907,596 3/1990 Schmid et al. .
4,919,121 4/1990 Rydell et al. .
4,936,310 6/1990 Engström et al. .
4,940,459 7/1990 Noce .
4,952,205 8/1990 Mauerer et al. .
5,004,472 4/1991 Wallace .
5,009,662 4/1991 Wallace et al. .
5,019,041 5/1991 Robinson et al. .
5,021,046 6/1991 Wallace .
5,024,668 6/1991 Peters et al. .
5,084,060 1/1992 Freund et al. .
5,135,488 8/1992 Foote et al. .

ELECTRONICALLY MONITORED ANGIOPLASTY SYSTEM

FIELD OF THE INVENTION

This invention relates to angioplasty systems and more particularly, to electronically monitored angioplasty systems.

BACKGROUND OF THE INVENTION

Angioplasty systems are well known. A typical system includes a syringe coupled to a balloon catheter to be placed in a patient's blocked artery or the like. The balloon is inserted into an artery or vein and manipulated by a physician through the vascular system until the balloon is in the vicinity of the blockage. Fluid is then forced from the syringe into the balloon to inflate the balloon and compress the material blocking the artery against the walls of the artery to unblock the blood vessel. The balloon is then deflated and removed from the patient.

It has long been appreciated that to avoid injury to the patient the angioplasty balloon should not be inflated for too long a period of time or to too great a pressure. To monitor the pressure in the balloon, electronic monitors have been used with angioplasty systems that digitally display the pressure, typically in atmospheres, within the balloon as sensed by an electronic pressure transducer placed in fluid communication with the balloon. The electronic pressure transducer generates an electrical pressure signal corresponding to the pressure in the balloon. The electrical pressure signal is coupled over wires to conversion circuitry in the electronic monitor which typically compares the electric pressure signal to a reference value with the difference therebetween being representative of the actual pressure in the balloon. The conversion circuitry converts that difference into a numerical value for display on the digital numerical read-out.

One drawback with such conventional electronic angioplasty systems is the inability to verify that the conversion circuitry is working properly and thus that the displayed pressure is correct. While systems for blood pressure transducers have been developed to test the reliability of the wires to the monitor and of the pressure transducer itself in its operating environment, such as that disclosed in U.S. Pat. No. 4,760,730, systems to verify operation of the monitor's conversion circuitry is typically not usable in the operating environment of the angioplasty system. Such testing is inconvenient and removes the monitor from use for possibly a significant period of time. For example, to verify the operation of the conversion circuitry, the entire monitor usually must be sent to an electronics lab for testing.

Another drawback with such conventional electronically monitored angioplasty systems is that the physician must watch the pressure read-out to confirm that the balloon is completely deflated. For example, to avoid ischemia or other problems associated with extended pressure times or high pressures, the angioplasty balloon needs to be deflated to relax the blood vessel. Conventional systems require the physician to avert his attention to the pressure display to confirm balloon deflation which means the doctor risks being at least temporarily unaware of the patient's appearance or condition.

SUMMARY OF THE INVENTION

The present invention provides an electronically monitored angioplasty system which overcomes the above-mentioned drawbacks. In accordance with one aspect of the present invention, a verifier circuit is provided which allows for testing of the conversion circuitry even while the angioplasty system is in use. To this end, and in accordance with the broadest principles of the present invention, actuation of the verifier circuit induces a predetermined offset in the difference between the electrical pressure signal from the transducer and the reference signal used to determine the actual pressure in the balloon. This offset may be brought about by switching between two selected reference values depending upon whether the verifier circuit is actuated. Because the amount of offset is thus known, actuation of the verifier circuit should cause the displayed pressure value to change by a known amount, such as ten atmospheres. If the change in the read-out does not respond accordingly, then the conversion circuitry is not working properly and corrective actions may be taken. However, because the only effect of the verifier circuit is to offset the displayed value by a known increment, the verifier circuit may be actuated at any time to test the system, even in the midst of an angioplasty procedure, all without interfering with the otherwise normal use of the angioplasty system or the doctor's operation thereof.

In accordance with a further aspect of the invention, there is provided a pleasant audible indicator such as a series of short duration beeps when the balloon has been deflated so that it becomes unnecessary for the doctor to divert attention from the patient to learn that the pressure in the balloon has dropped below a predetermined threshold that indicates the balloon is deflated. To this end, the pleasant audible indicator is activated when the electrical pressure signal rises above and then falls below the predetermined threshold pressure. The threshold pressure may be the sum of a signal corresponding to the ambient pressure in the room and a predetermined pressure such as approximately 0.5 to 1 atmosphere.

By virtue of the foregoing, there is provided an angioplasty monitoring system that permits selective verification that the displayed pressure is accurate and that the monitor is operating correctly. Further, the monitor provides an audible indication that the pressure in the balloon has dropped below the threshold pressure without requiring the doctor to unnecessarily avert attention from the patient.

These and other objects and advantages of the present invention shall be made apparent by reference to the following description taken in conjunction with the accompanying drawings.

BRIEF DESCRIPTION OF THE DRAWINGS

The accompanying drawings, which are incorporated in and constitute a part of this specification, illustrate embodiments of the invention and, together with the general description given above, and the detailed description given below, serve to explain the principles of the invention.

DETAILED DESCRIPTION OF THE INVENTION

Figure 1:
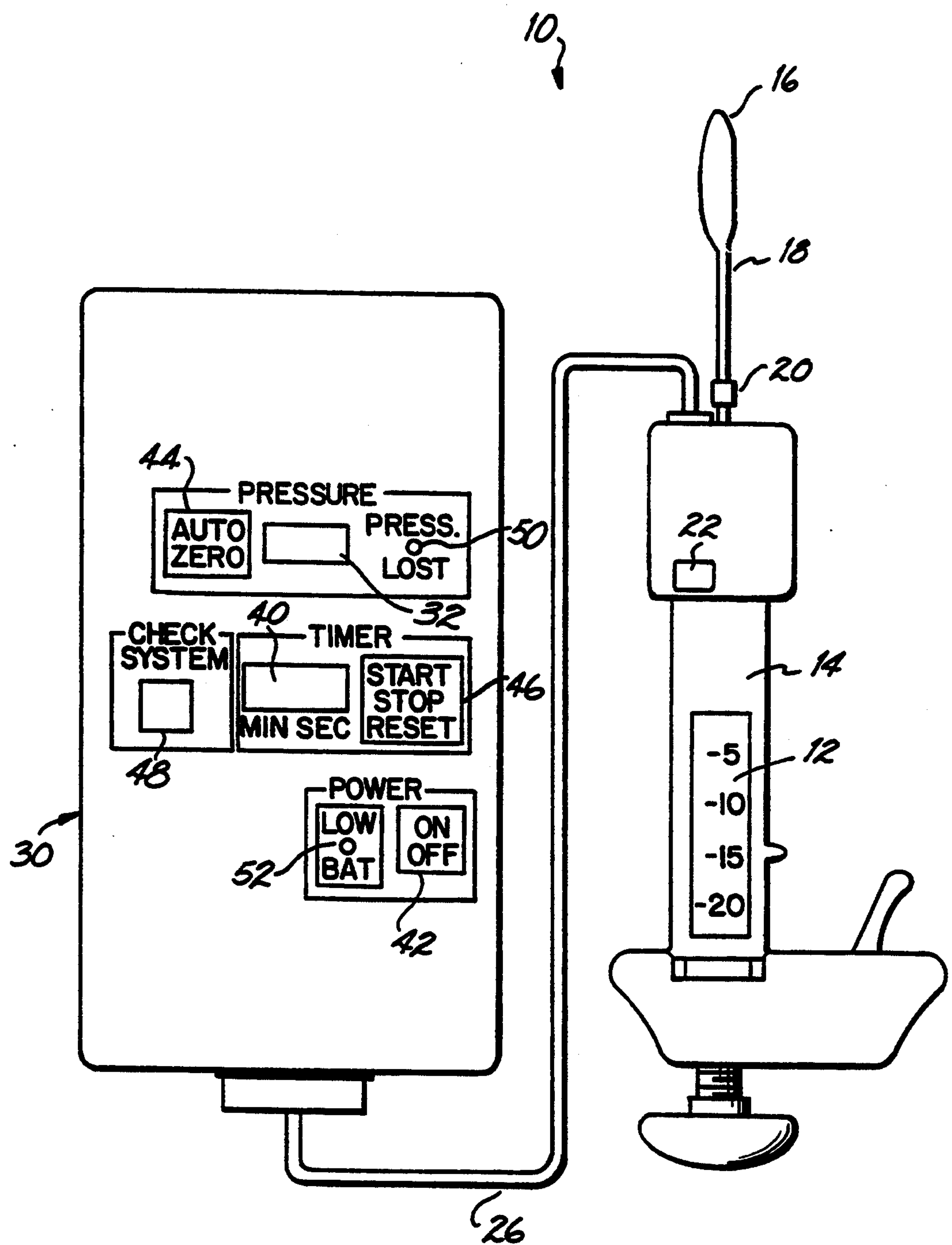
FIG. 1 is a diagrammatic illustration of an electronically monitored angioplasty system in accordance with the principles of the present invention.

An electronically monitored angioplasty system 10 is shown in FIG. 1. System 10 includes an angioplasty syringe 12 in a housing 14 for inflating and deflating a balloon 16 at the distal end of a balloon catheter 18 coupled to outlet 20 of the syringe 12. Mounted within the housing 14 to be in fluid communication with the syringe 12 and the catheter 18 is an electronic pressure transducer 22 for providing an electronic pressure signal 24 (see, e.g., FIG. 2) corresponding to the pressure in the catheter 18 and hence the balloon 16. The electronic pressure signal 24 is coupled by cable 26 to conversion circuitry 28, 28' and 28'' (see FIGS. 2, 3 and 4, respectively) within electronic monitor module 30 that converts the electrical pressure signal 24 to numerical values for display on digital read-out 32 of module 30. Typically, the numerical values displayed on the read-out 32 are in units of atmospheres. Alternatively, the numerical values may be displayed in units of pounds per square inch (psi) or the module 30 may be provided with a switch (not shown) that may be used to select whether the numerical values may be displayed in atmospheres or psi.

Module 30 includes a second digital readout display 40 to display the elapsed time for each angioplasty procedure, a plurality of switches (power on/off switch 42, auto zero switch 44, timer reset switch 46, and pressure test switch 48), and a balloon deflated LED 50, all for purposes to be described. Module 30 may also be operated under battery power and a circuit provided which monitors the battery voltage level. When the battery level falls below a predetermined level that indicates the battery may be failing, the low battery LED is illuminated to alert the operator to the battery condition.

Figure 2:
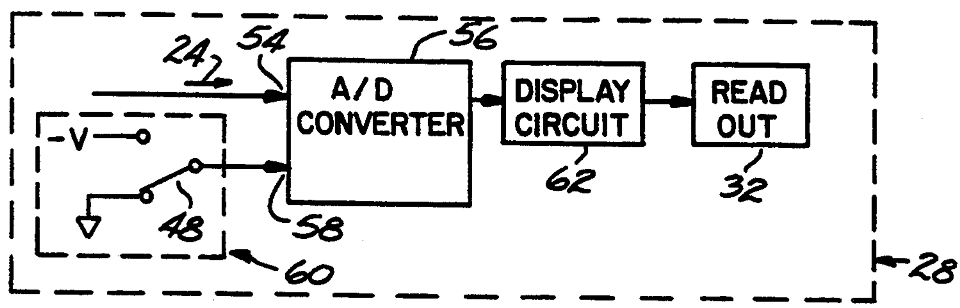
FIG. 2 is a block diagram of one embodiment of a pressure conversion circuit for the electronic monitor of the system of FIG. 1.

One embodiment constructed in accordance with the principles of the present invention is shown in FIG. 2. The pressure signal 24 from the pressure transducer 22 is coupled to the positive input 54 of an analog-to-digital (A/D) converter 56. The reference input 58 of the A/D converter 56 is coupled to a verifier circuit 60 that supplies one of two reference signals through the pressure test switch 48. The digital value output by the converter 56 is coupled to a display circuit 62 that drives the digital read-out 32 to display the numerical value corresponding to the digital value from the converter 56. The pressure test switch 48 normally couples an electrical ground to the reference input 58 of the converter 56 so the digital value corresponds to the difference between the electrical pressure signal 24 and electrical ground. The displayed numerical value corresponding to this digital value also corresponds to the pressure sensed in the balloon.

To verify the operation of the A/D converter 56 and the display circuit 62, the pressure test switch 48 is moved to the second position which couples the reference input 58 of the A/D converter 56 to a second reference signal −V from verifier circuit 60. In this position, the A/D converter 56 produces a digital value that corresponds to the electrical pressure signal 24 offset by the level of the second reference signal −V. Display circuit 62 uses the offset digital value from the converter 56 to display a numerical pressure value offset by a predetermined amount that corresponds to the difference between the second reference signal −V and electrical ground. Preferably, the reference signal −V source has a voltage magnitude relative ground such that the predetermined amount corresponds to a displayed numerical value of 10 plus or minus 0.5 atmospheres.

Observing a change in the displayed numerical value on the read-out 32 by this predetermined amount confirms the proper operation of the pressure conversion circuit 28 any time the verifier circuit 60 is activated by the pressure test switch 48. Deactivating the verifier circuit 60 by returning pressure test switch 48 to the first position, recouples the electrical ground to the reference input 58 and causes the numerical value displayed on read-out 32 to correspond to the balloon pressure sensed by the transducer.

Figure 3:
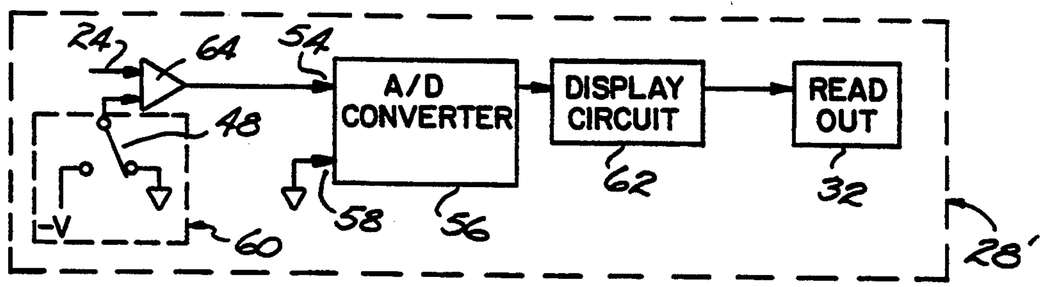
FIG. 3 is a block diagram of a second embodiment of a pressure conversion circuit for the electronic monitor of the system of FIG. 1.

With reference to FIG. 3, another embodiment of a pressure conversion circuit 28' is shown. Conversion circuit 28' is similar to conversion circuit 28 but further includes a differential amplifier 64 that couples the verifier circuit 60 to the electrical pressure signal 24. The output of the differential amplifier 64 is coupled to the positive input 54 of the A/D converter 56 for conversion to a digital value that is used by the display circuit 62 to generate the numerical value displayed on the digital read-out 32. The reference input 58 of the converter 56 remains coupled to electrical ground in the conversion circuit 28'. The verifier circuit 60 is as described previously. The pressure test switch 48 is normally in the position shown in FIG. 3 to connect electrical round to one input of the differential amplifier 64. In this position, the differential amplifier 64 passes the electrical pressure signal 24 to the A/D converter 56 without change so the converter 56 produces a digital value that corresponds to the pressure in the balloon 14.

To verify the operation of the conversion circuit 28' the pressure test switch 48 is moved so the second reference signal is coupled to the differential amplifier 64. In this position, the differential amplifier 64 shifts the electrical pressure signal by the difference between electrical ground and the second reference signal. The shifted electrical pressure signal is coupled to the A/D converter 56 which produces a digital value that is used by the display circuit 62 to display a numerical value that corresponds to the pressure in the balloon offset by the predetermined amount. Preferably, the second reference signal −V has a voltage magnitude relative to ground so that the predetermined amount corresponds to a displayed numerical value of 10 plus or minus 0.5 atmospheres.

Observing a change in the displayed value on the read-out 32 by this predetermined amount confirms the proper operation of the pressure conversion circuit 28' any time the verifier circuit 60 is activated by moving the pressure test switch 48 to the second position. Deactivating the verifier circuit 60 by returning pressure test switch 48 to the first position re-couples the electrical ground to the differential amplifier 64 and causes the numerical value displayed on read-out 32 to correspond to the balloon pressure sensed by the transducer.

Figure 4:
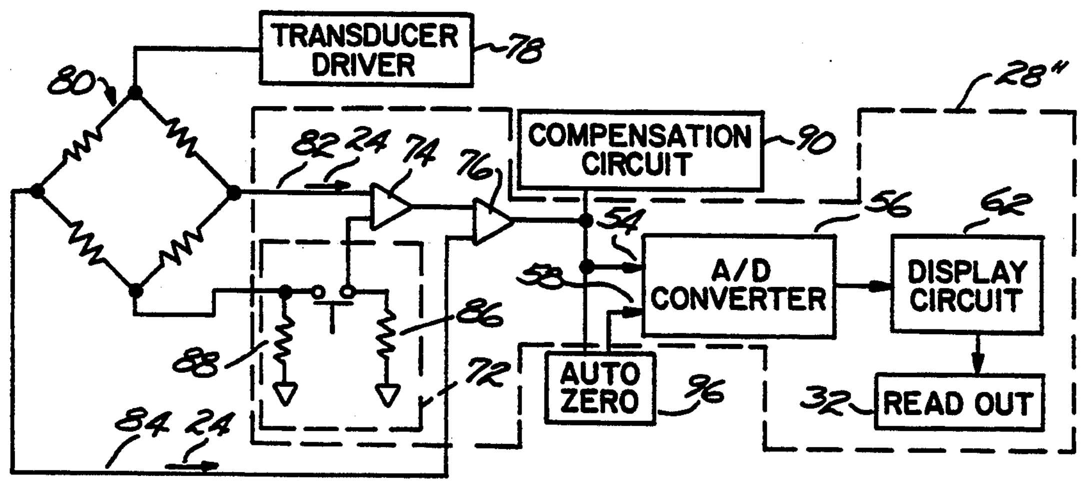
FIG. 4 is a schematic diagram of a third embodiment of a pressure conversion circuit embodying the principles of the present invention.

A still further embodiment of a pressure conversion circuit 28" is shown in FIG. 4 and includes a verifier circuit 72, differential amplifiers 74, 76, the A/D converter 56, the display circuit 62 and the digital read-out 32. This embodiment also includes a transducer driver circuit 78 for electrically activating a resistor bridge transducer 80 which is preferably manufactured by Sensyn, Inc. of Sunnyvale, Calif. and is designated Part No. SCC500AH. The electrical pressure signal 24 from the transducer 80 has two components 82, 84 of which electrical pressure signal component 82 is coupled to one input of the differential amplifier 74 and the other electrical pressure signal component 84 is coupled to one input of the differential amplifier 76. Verifier circuit 72 is coupled to the other input of the differential amplifier 74 and the output of amplifier 74 is coupled to the remaining input of the amplifier 76.

With the pressure test switch 48, in the position shown in FIG. 4, electrical ground is coupled through resistor 86 to the differential amplifier 74 and the electrical pressure signal component 82 is unchanged by the differential amplifier 74. The output of the differential amplifier 74 is coupled to the input of the differential amplifier 76 which has its other input coupled to the other electrical signal component 84. The output of the differential amplifier 76 is the difference between the two electrical pressure signal components 82, 84 when the test pressure switch 48' is in the position shown in FIG. 4. This difference corresponds directly to the pressure sensed by the transducer 80 and is converted by the converter 56 which causes the display circuit 62 to display a numerical value on read-out 32 that corresponds to the pressure in the balloon.

The second reference signal of the verifier 72 is preferably produced by dropping the return current from the transducer 80 across a resistor 88. The resistor 88 is preferably sized to produce a reference signal at its high potential end that corresponds to a pressure of 10 atmospheres.

By selectively coupling the second reference signal from the verifier circuit 72 to the input of the differential amplifier 74, the output of the differential amplifier 74 becomes the electrical pressure signal component 82 offset by the second reference signal. The electrical pressure signal component 82 offset by the second reference signal causes the differential amplifier 76 to also change by an amount corresponding to the second reference signal. The digital value converted from the offset electrical pressure signal output from the differential amplifier 76 produces an offset in the displayed numerical value on read-out 32 that corresponds to the second reference signal when the conversion circuit 28" is working properly. Preferably, a change of $10\pm0.5$ atmospheres in the displayed value on the read-out 32 verifies that the conversion circuit 28" is properly working. To return to the display of the pressure within the balloon, switch 48' is permitted to return to its normally open position which re-couples electrical ground to the input of the differential amplifier 74.

Figure 5:
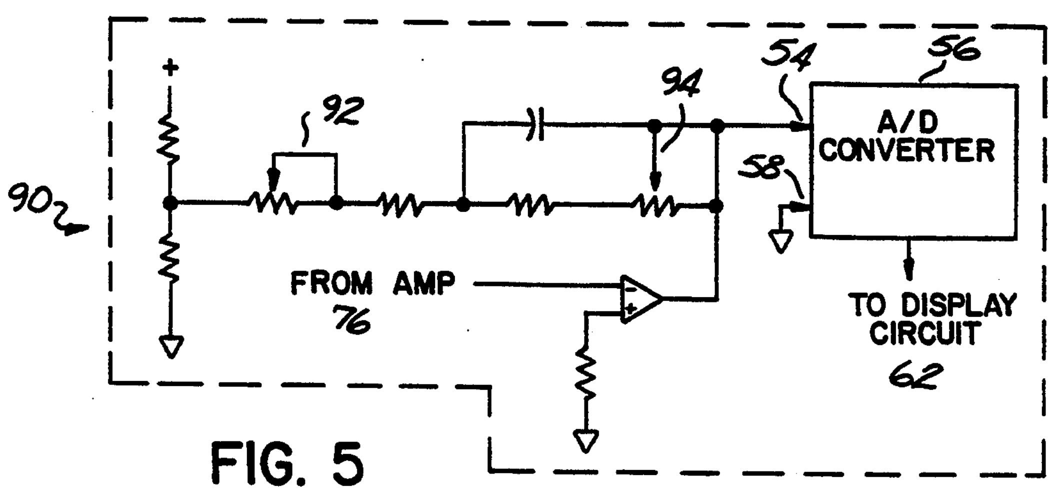
FIG. 5 is a schematic diagram of the compensation circuit shown in FIG. 4.

Preferably, the output of the differential amplifier 76 is compensated by a compensation circuit 90 that ensures the electrical pressure signal converted by operational range of pressures sensed by the pressure transducer 80. A compensation circuit used to practice the invention with the preferred pressure transducer 80 is shown in FIG. 5. Such circuits are well known in the art. The potentiometers 92, 94 in the compensation circuit 90 are adjusted in the electronics module 30 at the point of assembly by using a signal emulating the pressure signal from a pressure transducer calibrated in accordance with its manufacturer's specifications, such as the pressure transducer previously disclosed.

Figure 6:
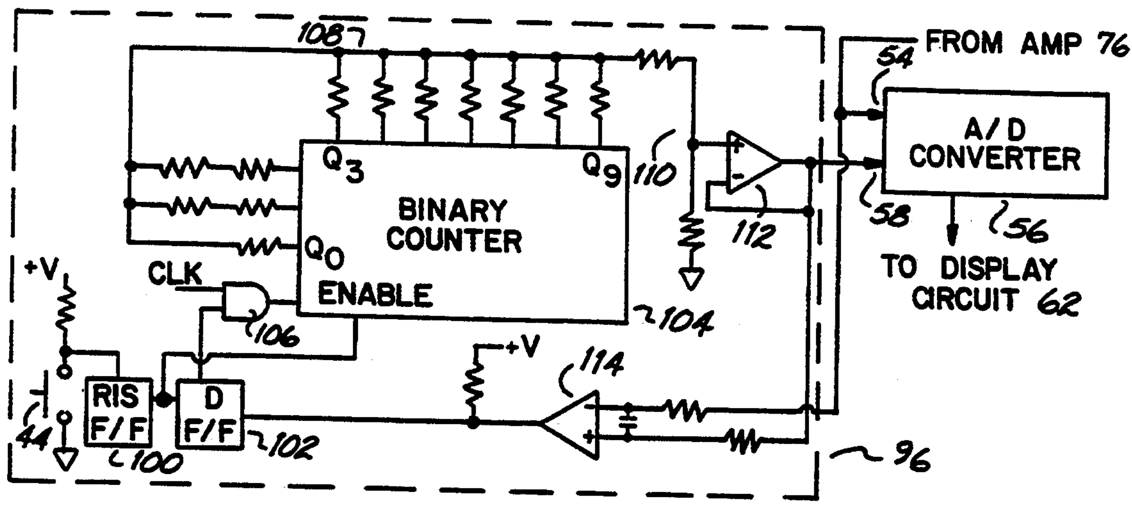
FIG. 6 is a schematic diagram of an auto-zero circuit used to establish the reference signal for the conversion circuit shown in FIG. 4.

Preferably, the reference input 58 of the A/D converter 56, shown in FIG. 4, is coupled to an auto-zero circuit 96 such as the one shown in FIG. 6. The auto-zero switch 44 selectively couples electrical ground to the set input of a R-S flip-flop 100. The Q output of the flip-flop 100 is coupled to the input of a D flip-flop 102 and to an enable input of a binary counter 104. The Q output of the D flip flop 102 is coupled to one input of a dual input AND gate 106 that has its other input tied to a clock signal, which is preferably 2048 Hz. Outputs Q0–Q9 are tied to a common point 108 through resistors tied to these outputs. The common point 108 supplies a voltage to a voltage divider 110 having its output coupled to the noninverting input of an operational amplifier 112. The output of the operational amplifier 112 is coupled to the reference input 58 of the A/D converter 56 and back to the inverting input of the operational amplifier 112. The output of the operational amplifier 112 is also coupled to an input of a comparator 114 having its other input coupled to the electrical pressure signal from amplifier 76 to be converted by the A/D converter 56. The output of the comparator 114 is tied to the reset input of the D flip-flop 102.

When the auto-zero switch 44 of FIG. 6 is depressed to couple electrical ground to the set input of the R-S flip-flop 100, the Q output of the R-S flip-flop goes to a logic high state which enables the binary counter 104 to count pulses and also transitions the input of the D flip-flop 102 to set the Q output of the D flip-flop 102 to a logic high. The logic high on the Q output of the D flip-flop 102 enables the AND gate 106 to couple the clock pulses on its other input to the binary counter 104. The counter 104 provides a sequential binary count on its outputs Q0–Q9 in response to the input of the clock signal from AND gate 106. The binary count on Q0–Q9 selectively varies the signal level and corresponding signal level at the common point 108. As the signal at the common point 108 varies so does the output of the voltage divider 110 that is coupled through the operational amplifier 112 to the reference input 58 of the A/D converter 56. The output of the operational amplifier 112 is also coupled to one of the inputs of the comparator 114 along with the electrical pressure signal to be converted on the other input of the comparator 114.

As long as the signal corresponding to the varying electrical signal from the binary counter 104 is less than the output from the amplifier 76, the output of the comparator 114 remains a logic low. When the varying signal from the binary counter 104 is slightly greater than the output of the amplifier 76, the output of the comparator goes to a logic high to reset the D flip-flop 102. Resetting the D flip-flop 102 causes its Q output to go low which disables the AND gate 106 from passing the clock pulses through to the counter 104. Thus, outputs Q0–Q9 of the counter 104 remain at the state corresponding to the last counted pulse and the signal at the common point 108 and the voltage divider 110 remains unchanged. Correspondingly, the output of the operational amplifier 112 remains unchanged so the reference signal to the reference input 58 of the A/D converter 56 remains the same.

When the catheter 18 is vented to the room pressure and the auto-zero switch 44 is depressed, the operation of auto-zero circuit 96 causes the signal at the reference input 58 to reach a value where it equals the pressure signal to be converted. Because the difference between the reference input 58 and the pressure signal at 54 is zero, the digital value from the A/D converter 56 is displayed as a numerical pressure value of zero on the digital read-out 32. Thus, the reference signal from the auto-zero circuit 96 to the reference input 58 is set to a value corresponding to the ambient pressure in the room plus a transducer offset voltage. By releasing the switch 44 and closing the catheter 18 from the room pressure, the balloon pressure is measured with reference to the ambient pressure in the room which corresponds to a numerical read-out of zero atmospheres.

Figure 7:
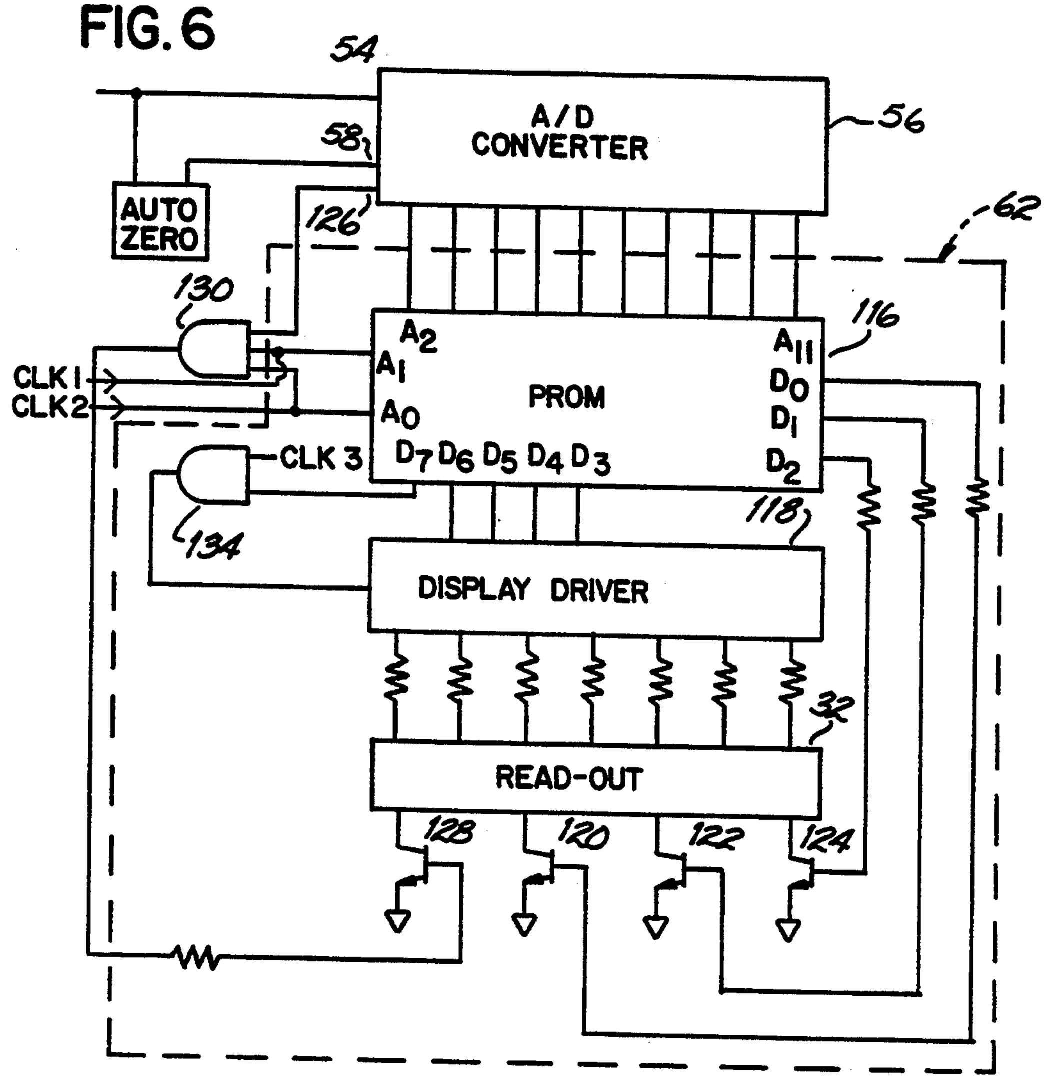
FIG. 7 is a schematic diagram of the display circuitry for the electronic monitor of the system in FIG. 1.

The display circuitry 62 is shown in FIG. 7 and includes a programmable read-only memory (PROM) 116, a segment display driver 118, and the digital read-out 32. Preferably, digital read-out 32 has three segmented digits and a sign segment. Address lines $A_2$-$A_{11}$ of the PROM 116 are coupled to the digital output of the A/D converter 56 and the two least significant address bits $A_0$, $A_1$, are coupled to clock signals CLK1, CLK2. Four of the data outputs, $D_3$–$D_6$, of the PROM 116 are coupled to segment display driver 118. The data from PROM 116 on these four outputs correspond to the binary-coded decimal (BCD) digits to be displayed on the read-out 32. Data outputs $D_0$, $D_1$, $D_2$ are coupled to the base of three bipolar transistors 120, 122, 124, respectively. The transistors 120, 122, and 124 are used to select the digit in the digital read-out 32 to be illuminated. The polarity output 126 of the A/D converter 56 is coupled to a fourth bipolar transistor 128 through a triple input AND gate 130 to control the sign segment of the read-out 32. All of the collectors of the transistor 120, 122, 124, 128 are coupled to the digital read-out 32 and the emitters of the transistors are coupled to electrical ground.

To display pressure data, the digital output of the A/D converter 56 and the two clock signals coupled to the least significant address bits define an address and the data stored at the address is output to the display driver 118 and the transistors 120, 122, and 124. Of the three data outputs $D_0$, $D_1$, $D_2$ coupled to the transistors 120, 122, and 124, only one is logically active at a time to forward bias the base-emitter junction of one of the transistors which selects the segments of one digit in the read-out 32 for illumination. The segments of the selected digit are illuminated in accordance with the segment driving signals from display driver 118 which were derived from the four BCD data outputs on $D_3$–$D_6$ from the PROM 116. As the two least significant bits of the address lines $A_0$, $A_1$ of the PROM 116 change in accordance with the clock signals CK1, CLK2 the selected memory locations corresponding to the data on address lines $A_0$–$A_{11}$ provide BCD data on $D_3$–$D_6$ for each of the digits and the proper control bits on $D_0$–$D_2$ to select the corresponding digit for the pressure sensed in the balloon for illumination in the read-out 32. The sign segment of the read-out 32 is driven by the polarity bit 126 from the A/D converter 56 which is either a blank or minus sign. The clock signals coupled to the other two inputs of the AND gate 130 are used to "blink" the minus sign when it is activated.

Preferably, the most significant bit $D_7$ of the data stored within the PROM is a logic low for pressure values within the operational range of the system 10 (FIG. 1) which is preferably −1 atmosphere to +30 atmospheres. When the pressure exceeds the upper limit of this range, data stored in the PROM 116 corresponding to these higher pressures drives the most significant data bit $D_7$ output by the PROM 116 to a logic high. This bit is coupled to a dual input AND gate 134 which has its remaining input tied to a clock signal CLK3, which is preferably 2 Hz. The output of the gate 134 is coupled to the blanking input of the display driver 118. Preferably the BCD value stored in the PROM 116 for the three digits corresponds to an "8" for pressure values above a predetermined maximum pressure. Preferably, this predetermined maximum pressure is 34 atmospheres so the pressure read-out provides a blinking indication of the pressure sensed in the range of 30 to 34 atmospheres and provides a blinking "888" indication for pressures above 34 atmospheres.

Figure 8:
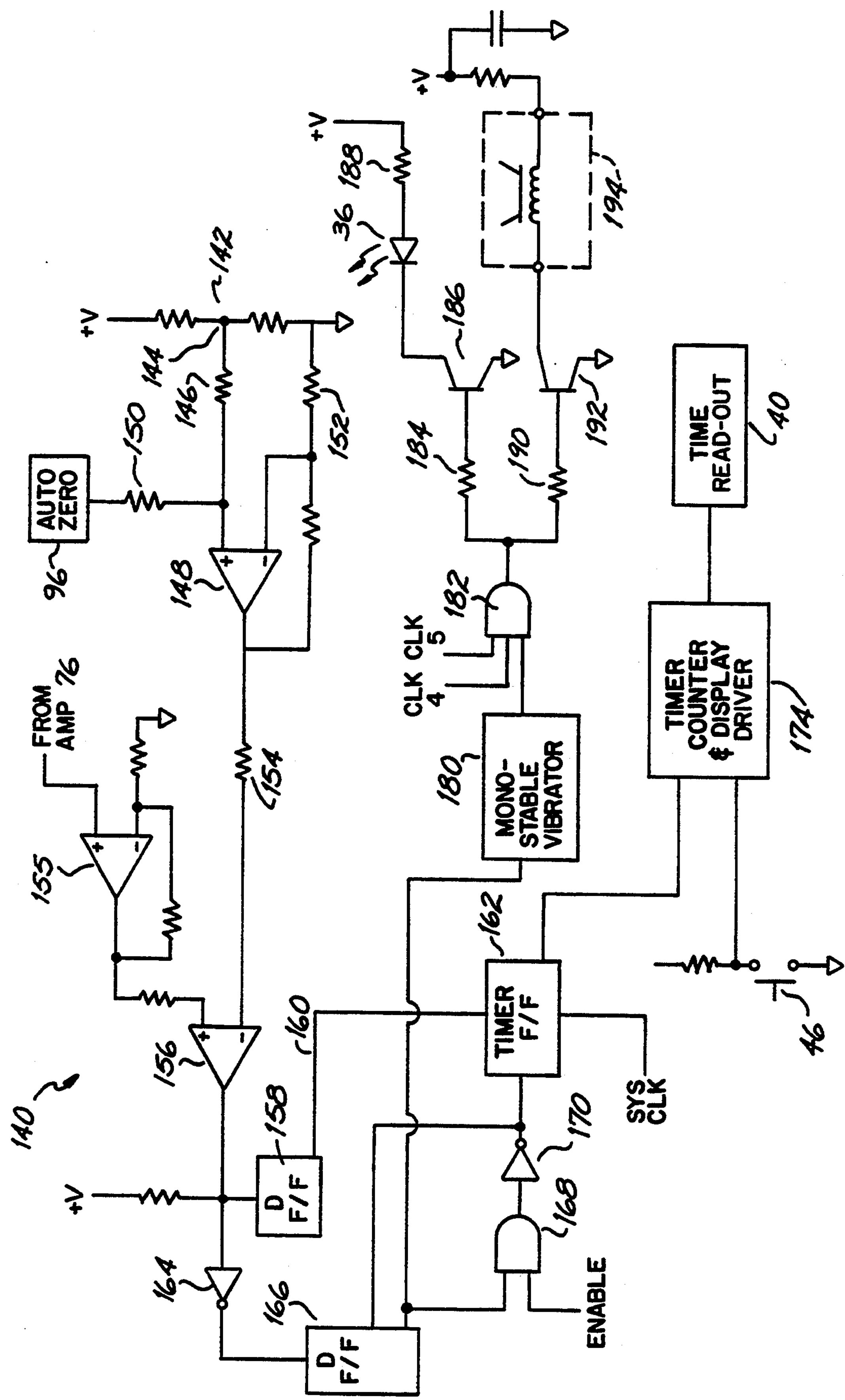
FIG. 8 is a schematic diagram of an embodiment of the audible balloon deflated indicator circuit of the system of FIG. 1.

An embodiment of the audible balloon deflation indicator circuit 140 of the present invention is shown in FIG. 8. The output of a voltage divider 142 provided at node 144 is coupled through a resistor 146 to an input of an operational amplifier 148. The auto-zero circuit 96 is coupled through a resistor 150 to the operational amplifier 148 so the voltage at node 144 and the voltage from the auto-zero circuit 96 are summed at the non-inverting input of the operational amplifier 148. The other input of the operational amplifier 148 is coupled to electrical ground through a resistor 152. The output of the operational amplifier 148 is coupled through a resistor 154 to one input of a comparator 156 which has its other input tied through a signal conditioning amplifier 155 to the electrical pressure signal from differential amplifier 76.

The output of the comparator 156 is coupled to a set input of a D flip-flop 158 which has its Q output 160 coupled to a reset input of another D flip-flop 162 used for the timer. The output of the comparator 156 in FIG. 8 is also inverted by an inverter 164 and its output is coupled to a set input of a D flip-flop 166. The Q output of the D flip-flop 166 is coupled to one input of a dual input AND gate 168 that has its other input tied to an enable signal from the system timer circuit. The output of the gate 168 is inverted by inverter 170 and is used to reset D flip-flop 166 and enable timer flip-flop 162. The output from the inverter 170 and the D flip-flop 160 are used to control timer flip-flop 162 for selectively permitting the system clock pulses to pass through to the timer counter and display driver 174. Timer reset switch 46 is used to reset the timer count and clear the timer read-out 40 through the timer counter and display driver 174.

The output of flip-flop 166 is also used to activate a monostable vibrator 180. The output of the monostable vibrator 180 is coupled to one input of a three input AND gate 182 and the remaining two inputs of the AND gate 182 are coupled to clock signals CLK4, CLK5 which have different time periods. The output of the triple input AND gate 182 is provided through a resistor 184 to a base of an NPN transistor 186 having its collector tied to a cathode of the lamp LED 36. The anode of the LED 36 is tied to a +V voltage source through a resistor 188. The output of the AND gate 182 is also coupled through a resistor 190 to a base of another NPN transistor 192 having its collector tied to a power voltage through an audio annunciator 194. The audio annunciator 194 is preferably designated by Part No. AT11K and is produced by Products Unlimited of Dayton, Ohio.

The signal present at the input of the operational amplifier 148 from the voltage divider 142 and the auto-zero circuit 96 constitutes a threshold signal to the operational amplifier 148. This threshold signal is the sum of the fixed value from the voltage divider 142 and the reference signal provided by the auto-zero circuit 96 as previously discussed. Thus, the threshold signal is preferably a signal indicative of the ambient pressure in the angioplasty procedure room plus a predetermined voltage. Preferably, the predetermined voltage from the voltage divider 142 corresponds to a numerical pressure value of 0.5–1 atmosphere. The output of the operational amplifier 148 couples the threshold voltage to the comparator 156 so the output of the comparator 156 goes to a logic high when the electrical pressure signal to be converted exceeds the threshold voltage. This logic high sets the D flip-flop 158 which in turn sets the D flip-flop 162 which permits the clock pulses to be passed by flip-flop 162 so they may be counted by the timer counter and display driver 174. Thus, when the pressure in the balloon exceeds the threshold signal, the timer clock signal is passed to the timer counter and display driver 174 so an elapsed time count is initiated and the elapsed time of balloon inflation is displayed on the timer read-out 40, preferably in seconds.

When the electrical pressure signal to be converted falls below the threshold signal present at the input of the comparator 156, the output of the comparator 156 goes to a logic low, which causes the output of the inverter 164 to go high which causes flip-flop 166 to change state. The $\overline{Q}$ output of the D flip-flop 166 causes AND gate 168 and inverter 178 to change state. This resets the timer flip-flop 162 to disable the passing of the system clock pulses. Thus, when the pressure falls below the threshold signal, the balloon is considered to be deflated and the elapsed time remains unchanged until reset by the timer reset switch 46.

The output of the comparator 156 is also inverted by the inverter 164 to a logic high when the pressure signal to be converted falls below the threshold at the input of the comparator 156. This sets the D flip-flop 166. The Q output of the D flip-flop 166 activates the monostable vibrator 180 which provides a logic high pulse for a predetermined period of time to the triple input AND gate 182. During this predetermined time period, the AND gate 182 provides a signal that varies in accordance with clock signals CLK4, CLK5 which intermittently turn on the transistors 186 and 192. This intermittent activation of the two transistors 186 and 192 causes the LED 36 and the audio annunciator 194 to be intermittently driven. Thus, the LED 36 provides a flashing indication that the balloon pressure is below the threshold while the audio annunciator circuit 194 is intermittently driven to produce a series of pleasant audible beeps to indicate the balloon pressure is below the threshold.

Prior to operation, the physician connects the module 30 to a calibrator which includes a fixed resistor bridge network and a precision resistor in parallel connection. The precision resistor is selectively connected to ground through a calibration switch. When the switch is depressed the grounding of the precision resistor unbalances the bridge by a precise amount which is preferably indicated by a read-out of 20 atmospheres on the read-out 32. Such calibration techniques are well-known. A display of 20±0.5 atmospheres on the digital read-out 32 verifies that the electronic module 30 is in calibration. If the display does not verify the calibration of the module 30 then the module should be discarded. To further verify the module 30, the pressure test switch 48 may be depressed while the calibration switch is depressed and if the calibration reading increases by the predetermined amount, say 10 atmospheres, the operation of the module has been verified for a higher range of pressure.

In operation, the physician connects the cable 26 between the housing 14 and the module 30 and turns on power by pressing the power on/off button 42. Following a warm-up period, a stopcock at the outlet 20 is turned to vent the syringe 12 and balloon catheter 18 to the atmosphere in the angioplasty room and the auto-zero switch 44 is momentarily depressed. Once the pressure display 32 settles to a zero pressure reading, the stopcock is closed. The doctor may also depress and temporarily hold the timer re-set switch 46 to reset the elapsed time display to zero seconds.

To fill the syringe 12 with the media for inflating the balloon 16, the outlet 20 onto which the catheter 18 is later fitted is inserted into a container of the contrast media. By withdrawing the plunger of the syringe 12 rearwardly, the media is pulled into the syringe. The plunger portion may be locked to hold the media within the syringe by releasing the trigger on the housing 14. The syringe is then turned upright and the plunger incrementally advanced by rotating the plunger knob to purge air from the syringe 12. This procedure may be repeated if additional media is desired.

To verify the operation of the pressure conversion and display circuitry, the doctor may depress the pressure test switch 48 and observe the pressure value displayed on the read-out 32. If the displayed value increases by 10 atmospheres while the button 48 is depressed, the physician knows the pressure conversion circuit is working correctly. Otherwise, the doctor knows the module 30 or cable 26 is defective and may discard the module and wire.

Once the doctor is satisfied the system is working properly, the balloon 16 and catheter 18 may be injected into the vascular system of the patient and manipulated to the blockage site. The balloon may then be inflated by expelling the fluid from within the syringe. As the pressure increases, the timer counter/display driver 174 begins counting clock pulses and the timer display 40 shows an elapsed time while the pressure value displayed on the pressure read-out 32 begins to increase from zero. The doctor, at any time, may stop the expulsion of the fluid from the syringe to stabilize the pressure displayed and depress the pressure test switch 48. After confirming that the displayed pressure value increases by 10 atmospheres, the button 48 may be released so the displayed pressure returns to the previous reading and the balloon inflation resumed.

Once the pressure has reached a maximum level selected by the doctor, the balloon may be deflated by withdrawing the fluid into the syringe 12. Again at any time, the doctor may verify the operation of the pressure conversion circuit by depressing the pressure test switch 48. When the pressure within the balloon falls below the threshold pressure, the audible balloon deflation indicator circuit 140 sounds a pleasant audible indicator for a short duration to inform the doctor that the pressure within the balloon has fallen below the threshold pressure without disturbing the doctor or diverting her attention. The elapsed time may be observed on the time display 40. To initiate another angioplasty procedure, the doctor clears the elapsed time by depressing and temporarily holding the timer reset switch 46 and begins another inflation cycle. Preferably, the timer may be reset by a signal exceeding the threshold voltage to ensure the timer is reset for the next inflation cycle.

While a preferred embodiment of the present invention has been described, further modifications and changes would be apparent to one of ordinary skill in the art without departing from the principles of the invention. For example, the A/D converter 56 may be replaced with a voltage to frequency converter. To modify the displayed numerical value by a predetermined amount, a frequency counter could be preset with a known number that corresponds to a known pressure amount. It is intended that all such changes and modifications obvious to one of ordinary skill in the art be covered by the appended claims.

What is claimed is:

1. An angioplasty system comprising:
an angioplasty syringe with an outlet connectable to a balloon catheter having a balloon to be inflated and deflated;
pressure transducer means mounted in fluid communication with the syringe outlet for generating an electrical pressure signal corresponding to the pressure in the balloon;
conversion circuit means coupled to said pressure transducer means for converting said electrical pressure signal to a numerical pressure value, said conversion circuit means including a read-out for displaying the numerical pressure value; and
verifier circuit means coupled to the conversion circuit means for selectively causing said conversion circuit means to offset the numerical pressure value by a predetermined amount whereby observing a change in the displayed numerical value on said read-out corresponding to said predetermined amount verifies operation of said conversion circuit means.

2. The system of claim 1 further comprising:
a module housing said conversion circuit means and said verifier circuit means; and
an electrical cable interconnecting-said module to said pressure transducer means whereby said module is separate from said syringe.

3. The system of claim 1 further comprising:
reference signal means for providing a first and a second reference signal;
switching means having a first position for coupling said first reference signal to said conversion circuit means and a second position for coupling said second reference signal to said conversion circuit means, said numerical pressure value being correlated to said electrical pressure signal and said reference signal provided by said reference signal means such that said numerical pressure value corresponds to said pressure in the balloon in response to said switching means being in said first position and said numerical pressure value corresponding to said pressure in the balloon offset by said predetermined amount in response to said switching means being in said second position.

4. The system of claim 3 further comprising:
a first differential means for providing a differential pressure signal, said differential pressure signal being coupled to said conversion circuit means;
said switching means being coupled to said differential means, said differential pressure signal correlates to said electrical pressure signal and said reference signal from said reference signal means such that said differential pressure signal corresponds to said pressure in the balloon in response to said switching means being in said first position and said differential pressure signal corresponds to electrical pressure signal offset by said predetermined amount in response to said switching means being in said second position.

5. The system of claim 4 further comprising:
said pressure signal from said pressure transducer means having first and second components;
said first differential means being coupled to said first pressure signal component; and
second differential means for providing a differential pressure component signal, said differential pressure component signal being coupled to said first differential means, said second differential means being coupled to said second pressure signal component generated by said pressure transducer and to said reference signal from said reference signal means, said differential pressure component signal relates to said second pressure signal component and said reference signal such that said differential pressure component signal corresponds to said second pressure signal component coupled to said second differential means in response to said switching means being in said first position and said differential pressure component signal corresponds to said second pressure signal component coupled to said second differential means offset by said predetermined amount in response to said switching means being in said second position whereby said differential pressure signal from said first differential means is selectively varied to offset the numerical pressure value by said predetermined amount to verify the operation of said conversion circuit means.

6. The system of claim 3, said second reference signal corresponding to approximately 10 atmospheres of pressure.

7. An electronic monitor for an angioplasty system having an angioptasty syringe with an outlet connectable to a balloon catheter terminating in a balloon to be inflated and deflated and a pressure transducer for generating an electrical pressure signal corresponding to the pressure in the balloon, the monitor comprising:
input means for receiving the signal from the pressure transducer; and
conversion circuit means coupled to the input means for converting the electrical pressure signal to a numerical pressure value, said conversion circuit means including a read-out for displaying the numerical pressure value; and
verifier circuit means coupled to the conversion circuit means for selectively causing said conversion circuit means to offset the numerical pressure value by a predetermined amount whereby observing a change in the displayed numerical value on said read-out corresponding to said predetermined amount verifies operation of said conversion circuit means.

8. The system of claim 7 further comprising:

said conversion circuit means and said verifier circuit means being housed in a module; and an electrical cable interconnecting said module to said pressure transducer whereby the electrical pressure signal is coupled to said conversion circuit-means housed in said module is separate from said syringe.

9. The system of claim 7 further comprising:

reference signal means for providing a first and a second reference signal;

switching means having a first position for coupling said first reference signal to said conversion circuit means and a second position for coupling said second reference signal to said conversion circuit means, said numerical pressure value being correlated to said electrical pressure signal and said reference signal provided by said reference signal means such that said numerical pressure value corresponds to said pressure in the balloon in response to said switching means being in said first position and said numerical pressure value corresponding to said pressure in the balloon offset by said predetermined amount in response to said switching means being in said second position.

10. The system of claim 9 further comprising:

a first differential means for providing a differential pressure signal, said differential pressure signal being coupled to said conversion circuit means;

said switching means being coupled to said differential means, said differential pressure signal correlates to said electrical pressure signal and said reference signal from said reference signal means such that said differential pressure signal corresponds to said pressure in the balloon in response to said switching means being in said first position and said differential pressure signal corresponds to electrical pressure signal offset by said predetermined amount in response to said switching means being in said second position.

11. The system of claim 10 further comprising:

said pressure signal from said pressure transducer means having first and second components;

said first differential means being coupled to said first pressure signal component; and second differential means for providing a differential pressure component signal, said differential pressure component signal being coupled to said first differential means, said second differential means being coupled to said second pressure signal component generated by said pressure transducer and to said reference signal from said reference signal means, said differential pressure component signal relates to said second pressure signal component and said reference signal such that said differential pressure component signal corresponds to said second pressure signal component coupled to said second differential means in response to said switching means being in said first position and said differential pressure component signal corresponds to said second pressure signal component coupled to said second differential means offset by said predetermined amount in response to said switching means being in said second position whereby said differential pressure signal from said first differential means is selectively varied to offset-the numerical pressure value by said predetermined amount to verify the operation of said conversion circuit means.

12. The system of claim 9, said second reference signal being a voltage corresponding to approximately 10 atmospheres of pressure.

13. A method for verifying operation of an angioplasty system having an angioplasty syringe connected to a balloon catheter terminating in a balloon to be inflated and deflated, comprising:

mounting a pressure transducer in fluid communication with the syringe;

generating an electrical pressure signal corresponding to the pressure in the balloon from the pressure transducer;

converting in conversion circuitry the electrical pressure signal to a numerical pressure value;

displaying the numerical pressure value; and verifying the operation of the conversion circuitry by selectively offsetting the numerical pressure value by a predetermined amount whereby observing a change in the displayed numerical pressure value on said read-out corresponding to said predetermined amount verifies said conversion circuit means.

14. The method of claim 13, said verifying step further comprising:

providing a first and a second reference signal, said second reference signal corresponding to said predetermined amount; and selectively coupling one of said provided reference signals to the conversion circuitry so that the displayed numerical value displayed on said read-out selectively corresponds to one of the pressure in the balloon and the pressure in the balloon offset by the predetermined amount.

15. The method of claim 13, said verifying step further comprising:

providing a first and a second reference signal, said second reference signal corresponding to said predetermined amount;

selectively coupling one of said reference signals to a differential means;

coupling the electrical pressure signal to the differential means so that said differential means generates a differential signal corresponding to the difference between the electrical pressure signal and the reference signal selectively coupled to said differential means; and coupling the differential signal to the conversion circuitry so that the displayed numerical value displayed on said read-out selectively corresponds to one of the pressure in the balloon and the pressure in the balloon offset by the predetermined amount.

16. The method of claim 15, further comprising:

generating first and second electrical pressure signal components from the transducer;

coupling one of the electrical pressure signal components to a first differential means and the other electrical pressure signal component to a second differential means;

providing a first and a second reference signal, said second reference signal corresponding to said predetermined amount;

selectively coupling one of said reference signals to a first differential means; and coupling a differential signal from said first differential means to the second differential means and a second differential signal from the second differential means to the conversion circuitry so that the displayed numerical value displayed on said readout selectively corresponds to one of the pressure in the balloon and the pressure in the balloon offset by the predetermined amount.

17. The method of claim 16, said reference signal providing step providing a voltage that corresponds to approximately 10 atmospheres of pressure.

* * * * *